United States Patent
Fraser et al.

(10) Patent No.: US 10,345,212 B2
(45) Date of Patent: Jul. 9, 2019

(54) CARRY OVER METER

(71) Applicant: Schlumberger Technology Corporation, Sugar Land, TX (US)

(72) Inventors: Laurence Fraser, Paris (FR); Francis Allouche, Le Plessis Robinson (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 861 days.

(21) Appl. No.: 14/108,306

(22) Filed: Dec. 16, 2013

(65) Prior Publication Data
US 2014/0182368 A1 Jul. 3, 2014

(30) Foreign Application Priority Data
Dec. 28, 2012 (EP) .................................... 12306711

(51) Int. Cl.
*G01N 9/36* (2006.01)
*E21B 43/34* (2006.01)
(Continued)

(52) U.S. Cl.
CPC ........... *G01N 9/36* (2013.01); *B01D 17/0208* (2013.01); *B01D 17/12* (2013.01);
(Continued)

(58) Field of Classification Search
CPC ...... E21B 43/34; E21B 47/0002; G01F 15/08; G01N 9/36
(Continued)

(56) References Cited

U.S. PATENT DOCUMENTS 4,539,023 A 9/1985 Boley
4,951,700 A * 8/1990 Kalman .................... G01F 1/74
137/174
(Continued)

FOREIGN PATENT DOCUMENTS

CA 2559701 C 10/2005
EP 1646849 B1 11/2008
(Continued)

OTHER PUBLICATIONS

Extended search report for the equivalent European patent application No. 12306711.8 dated Jun. 18, 2013.
(Continued)

*Primary Examiner* — Daniel S Larkin
*Assistant Examiner* — Anthony W Megna Fuentes
(74) *Attorney, Agent, or Firm* — Cameron R. Sneddon; Ron Embry, Jr.

(57) ABSTRACT

A separator is described as provided with a gas/liquid separator vessel, a sight glass, and a carry-over meter. The sight glass is positioned on the exterior of the gas/liquid separator vessel, and has a first inlet and a second inlet in fluid communication with a separation chamber of the gas/liquid separator vessel. The sight glass is further provided with a first outlet in fluid communication with the first inlet, and a second outlet in fluid communication with the second inlet. The sight glass has a tube extending between the first inlet and the second inlet with at least a portion of the tube being transparent to light in a visible range of wavelengths. The carry-over meter is provided with a first densitometer connected to the first outlet of the sight glass via piping and a second densitometer connected to the second outlet of the sight glass via piping.

18 Claims, 5 Drawing Sheets

(51) Int. Cl.
*E21B 47/00* (2012.01)
*B01D 17/12* (2006.01)
*B01D 17/02* (2006.01)
*B01D 19/00* (2006.01)

(52) U.S. Cl.
CPC .......... *B01D 19/0063* (2013.01); *E21B 43/34* (2013.01); *E21B 47/0002* (2013.01)

(58) Field of Classification Search
USPC ...................................... 73/323–334, 861.04
See application file for complete search history.

(56) References Cited

U.S. PATENT DOCUMENTS

| | | | |
|---|---|---|---|
| 5,029,482 | A | 7/1991 | Liu et al. |
| 5,497,665 | A | 3/1996 | Cage et al. |
| 5,526,684 | A * | 6/1996 | Liu .................... B01D 19/0057 73/200 |
| 5,535,632 | A * | 7/1996 | Kolpak .................... G01F 1/74 73/200 |
| 5,687,100 | A | 11/1997 | Buttler et al. |
| 6,318,156 | B1 * | 11/2001 | Dutton .................... E21B 43/36 73/61.44 |
| 6,327,915 | B1 | 12/2001 | Van Cleve et al. |
| 6,732,570 | B2 | 5/2004 | Francisco, Jr. |
| 6,857,315 | B1 * | 2/2005 | Mills ....................... G01F 23/02 116/227 |
| 7,523,639 | B2 | 4/2009 | Hays |
| 7,661,302 | B2 | 2/2010 | Gysling |
| 7,871,526 | B2 | 1/2011 | Allouche |
| 8,641,813 | B2 | 2/2014 | Gysling |
| 2002/0123852 | A1 | 9/2002 | Gysling et al. |
| 2006/0096388 | A1 | 5/2006 | Gysling et al. |
| 2007/0271070 | A1 | 11/2007 | Dmytriw et al. |
| 2008/0028822 | A1 | 2/2008 | Mattar |
| 2008/0053240 | A1 | 3/2008 | Henry et al. |
| 2008/0190195 | A1 | 8/2008 | Duffill et al. |
| 2010/0299089 | A1 | 11/2010 | Stack et al. |
| 2014/0076035 | A1 | 3/2014 | Henry |
| 2014/0090484 | A1 | 4/2014 | Henry et al. |
| 2014/0182368 | A1 | 7/2014 | Fraser et al. |
| 2014/0224006 | A1 | 8/2014 | Scott |
| 2014/0251026 | A1 | 9/2014 | Oddie |

FOREIGN PATENT DOCUMENTS

| | | |
|---|---|---|
| WO | 95/10028 | 4/1995 |
| WO | WO9605484 A1 | 2/1996 |
| WO | WO9831990 A1 | 7/1998 |
| WO | 01/31298 | 5/2001 |

OTHER PUBLICATIONS

Communication pursuant to Article 94-3 issued in the related EP Application 12306711.8, dated Sep. 29, 2016 (5 pages).
Roger.C. Baker, "Flow measurement handbook: Industrial Designs, Operating Principles, Performance and Applications—Coriolis Flowmeters," Chapter 17, Cambridge University Press, 2000, pp. 398-426.
G.M. Oddie and J.R.A. Pearson, "Flow rate measurement in two phase flow," Annual Review of Fluid Mechanics vol. 36, pp. 149-172.
"Mass flow meter," from Wikipedia at http://en.wikipedia.org/wiki/Mass_flow_meter.
Extended Search Report issued in the related EP Application 14000783.2, dated May 28, 2014 (9 pages).
Combined Search and Examination Report issued in the related GB Application 1515488.3, dated Feb. 17, 2016 (8 pages).
Extended Search Report issued in the related EP Application 12306712.6, dated Aug. 21, 2013 (7 pages).

* cited by examiner

CARRY OVER METER

BACKGROUND

During well testing operations, hydrocarbons flow at surface for a short period of time. Most of the well tests occur during exploration, appraisal, and initial completion of a well. As of today, the easiest way to dispose of unwanted hydrocarbons is to burn them. Oil and gas may be separated upstream of the burners/flares to allow an effective combustion.

Different types of separators exist on the market. One of the specificities of well testing operations is that they arise at the early stage of the life of a well. After drilling operations, reservoirs are contaminated with brines and other drilling fluids. Well testing separators may thus be able to handle multiphase flow of water, oil, and gas. Vertical separators have been used in the art as well as horizontal gravitational separators. Horizontal gravitational separators are believed to have better capabilities than vertical separators with regard to multiphase separation. The increasing demand, however, for enhanced rate gas/liquid separators presents diverse challenges.

The main constraint in designing a gas/liquid separator arises in the size and weight limits dictated by transportation authorities. By restricting the size of the separator vessel, gravitational capacities decrease, flow rate capacities decrease, and expected volumes decrease as well. To counteract this constraint, particular care may be given to the design of internal devices.

Internal devices, such as demisters can be made of a single demister element, which allows liquid components in natural gas to be captured, and the gas to pass through. However, increasing flow rates can decrease the efficiency of the single element demister. Demisters can also employ a second element to serve the same function after the gas passes through the first demister element. Mist extractors of this type may be seen in U.S. Pat. No. 4,539,023, where a ceramic mist extractor and a stainless steel mist extractor are described. The gas stream is forced to flow through a settling section where turbulence ends. In the settling section, the heavier liquids drop out and then the gas stream passes over a secondary tall baffle down through the primary ceramic mist extractor and ceramic chips or bodies therein and then upwardly over a tall baffle which forms a partition across the interior of the tank except an upper most portion thereof. The gas stream then flows downwardly through the stainless steel mist extractor. The ceramic mist extractor and the stainless steel mist extractor are horizontally oriented and segregated from each other in a formation that causes the gas stream to change direction in order to flow through the next element. The restricted gas flow through the mist extractors results in a pressure drop across the extractor material and causes them to operate at a lower temperature than that of the gas stream.

External devices such as sight glasses may be attached to separators in order to give visual confirmation of gas and liquid levels within the separator. Coriolis meters have been added to outlet pipes attached to separators in order to determine mass flow rates and densities of moving streams of gas and oil extracted by the separator in an attempt to determine the contents of the gas and oil extracted by the separator. However, Coriolis meters may have difficulty providing accurate mass flow rates and densities of gasses entrained with liquid. Further, it may be difficult to determine the content of the gasses separated by the separator and output through the Coriolis meter without further testing of gas samples.

SUMMARY

This summary is provided to introduce a selection of concepts that are further described in the detailed description. This summary is not intended to identify key or essential features of the claimed subject matter, nor is it intended to be used as an aid in limiting the scope of the claimed subject matter.

In one aspect, the present disclosure describes a separator. The separator is provided with a gas/liquid separator vessel having an exterior, a first end, a second end, an inlet, an outlet, and a separation chamber. The separator is also provided with a carry-over meter. The carry-over meter has a sight glass, a first densitometer, and a second densitometer. The sight glass is positioned on the exterior of the gas/liquid separator vessel, and has a first inlet and a second inlet in fluid communication with the separation chamber. The sight glass has a first outlet in fluid communication with the first inlet, and a second outlet in fluid communication with the second inlet, and a tube extending between the first inlet and the second inlet with at least a portion of the tube being transparent in a visible range of wavelengths. The first densitometer is connected to the first outlet and the second densitometer is connected to the second outlet of the sight glass.

In another aspect, the present disclosure describes a carry-over meter provided with a sight glass, a first densitometer, and a second densitometer. The sight glass has a first inlet, a second inlet, a first outlet in fluid communication with the first inlet, a second outlet in fluid communication with the second inlet, and a tube extending between the first inlet and the second inlet. At least a portion of the tube is transparent in a visible range of wavelengths. The first densitometer is connected to the first outlet and the second densitometer is connected to the second outlet.

In another aspect, the present disclosure describes a carry-over meter. The carry-over meter is provided with a first densitometer, a second densitometer, and piping. The first densitometer and the second densitometer positioned on a sight glass and in fluid communication therewith. The piping extends between the sight glass and the first and second densitometers, and between the first densitometer and the second densitometer to provide fluid communication between the first densitometer and the second densitometer.

BRIEF DESCRIPTION OF THE DRAWINGS

Certain embodiments of the present inventive concepts will hereafter be described with reference to the accompanying drawings, wherein like reference numerals denote like elements, and.

DETAILED DESCRIPTION

Specific embodiments of the present disclosure will now be described in detail with reference to the accompanying drawings. Further, in the following detailed description of embodiments of the present disclosure, numerous specific details are set forth in order to provide a more thorough understanding of the disclosure. However, it will be apparent to one of ordinary skill in the art that the embodiments disclosed herein may be practiced without these specific details. In other instances, well-known features have not been described in detail to avoid unnecessarily complicating the description.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Figure 1:
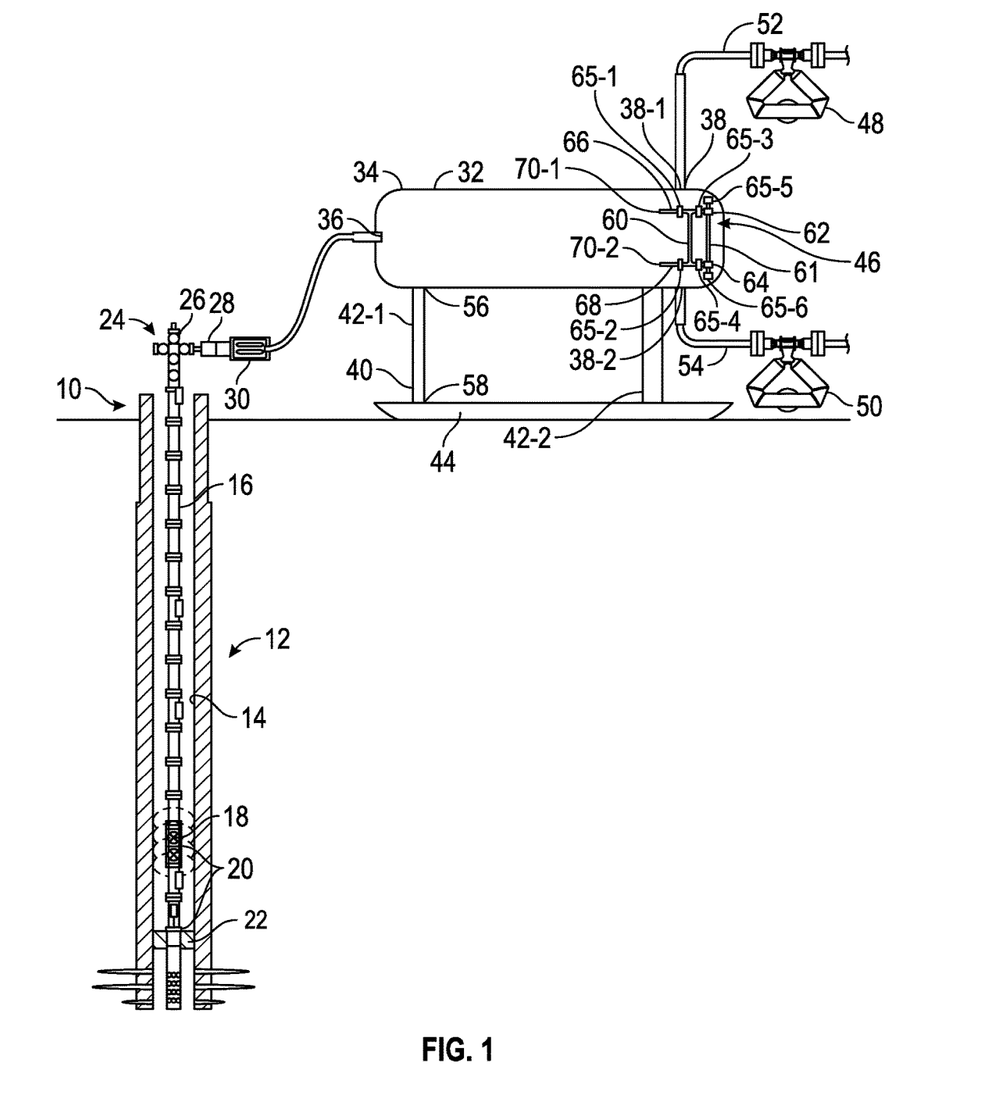
FIG. 1 is a schematic view of a well with a separator and a carry-over meter according to an embodiment of the present disclosure.

The present disclosure is particularly applicable to production and/or testing installations 10 (hereinafter "installations 10") such as are used in oil and gas wells or the like. FIG. 1 shows a schematic view of such an installation. In one embodiment, the installation 10 is composed of a well 12, which may contain steel casing 14, tubing 16, valves 18, downhole equipment 20, and a packer 22. Well head equipment 24, including a temporary production tree 26, may be located at the surface of the well 12. The temporary production tree 26 is connected to the tubing 16 for regulating and directing effluent coming out of the well 12. In the example of FIG. 1, the well 12 has been lined with the steel casing 14 (cased hole) in the conventional manner, although similar systems can be used in unlined (open hole) environments. The well head equipment 24 can include blow-out preventers, connections for fluid, power and data communication, and the production tree (or flow head) 26. An outlet valve of the production tree 26 can be connected to a choke manifold 28 where pressure and flow rate are controlled. Downstream of the choke manifold 28 may be located a heat exchanger 30 regulating the temperature of the effluent. From the heat exchanger 30, the effluent then flows into a separator 32 for the separation of oil, gas, and water, and further directs the flow from the well 12 to a distribution network of pipelines and tanks. Between the production tree 26 and the separator 32, a solids separator (not shown) may also be provided. In the particular application of the separator 32 to the oil industry, the separator 32 can be a three-phase separator that separates the multiphase effluent into single-phase streams of oil, gas, and water.

The separator 32 may be provided with a gas/liquid separator vessel 34, a first inlet 36, one or more outlet 38, support mechanisms 40 including stand elements 42-1 and 42-2, a frame 44, a carry-over meter 46, a first Coriolis meter 48, and a second Coriolis meter 50. The one or more outlet 38 may comprise a gas outlet 38-1 and an oil outlet 38-2. The gas outlet 38-1 may be connected to a gas outlet pipe 52 extending between the gas outlet 38-1 and the first Coriolis meter 48. The gas outlet pipe 52 may enable fluid communication between the gas/liquid separator vessel 34 and the first Coriolis meter 48. The oil outlet 38-2 may be connected to an oil outlet pipe 54 extending between the oil outlet 38-2 and the second Coriolis meter 50. The oil outlet pipe 54 may enable fluid communication between the gas/liquid separator vessel 34 and the second Coriolis meter 50. The stand element(s) 42-1 and 42-2 have a top side 56 and a bottom side 58 being supported by the frame 44.

The carry-over meter 46 may be positioned on the exterior of the gas/liquid separator vessel 34. The carry-over meter 46 may be used to determine liquid carry-over, an amount of liquid entrained in a separated gas within the gas outlet 38-1, by comparing the densities of dry gas, liquid, and the separated gas within the gas outlet 38-1. In one embodiment, the carry-over meter 46 may be provided with a sight glass 60, piping 61, a first densitometer 62, a second densitometer 64, and one or more valves 65-1-65-6. The carry-over meter 46 may be positioned on the exterior of the gas/liquid separator vessel 34 by connecting the carry-over meter 46 to a first piping 66 and a second piping 68 extending from a first outlet 70-1 and a second outlet 70-2, respectively. The first piping 66 and the second piping 68 may enable the sight glass 60 to be in fluid communication with the gas/liquid separator vessel 34, as will be described below. The first outlet 70-1 may be positioned at a level to provide fluid communication from the gas/liquid separator vessel 34 to the sight glass 60 of a separated gas within the gas/liquid separator vessel 34. The second outlet 70-2 may be positioned at a level to provide fluid communication from the gas/liquid separator vessel 34 to the sight glass 60 of a separated liquid within the gas/liquid separator vessel 34.

In another embodiment, the carry-over meter 46 may be provided with the piping 61, the first densitometer 62, the second densitometer 64, and the one or more valves 65-1-65-6. The carry-over meter 46 of this embodiment may be provided similarly to the carry-over meter 46 above with the exception that in this embodiment, the carry-over meter 46 does not include the sight glass 60. In this embodiment, the sight glass 60 is provided with valves 65-1 and 65-2 connected to the first and second piping 66 and 68, respectively, and valves 65-3 and 65-4 extending from the sight glass 60. In this embodiment, the carry-over meter 46 connects to the sight glass 60, which may already be connected to the gas/liquid separator vessel 34. This can be accomplished by connecting the piping 61 to the first densitometer 62, the second densitometer 64, and the valves 65-3 and 65-4, respectively, providing fluid communication between the sight glass 60 and the first and second densitometers 62 and 64.

Figure 2:
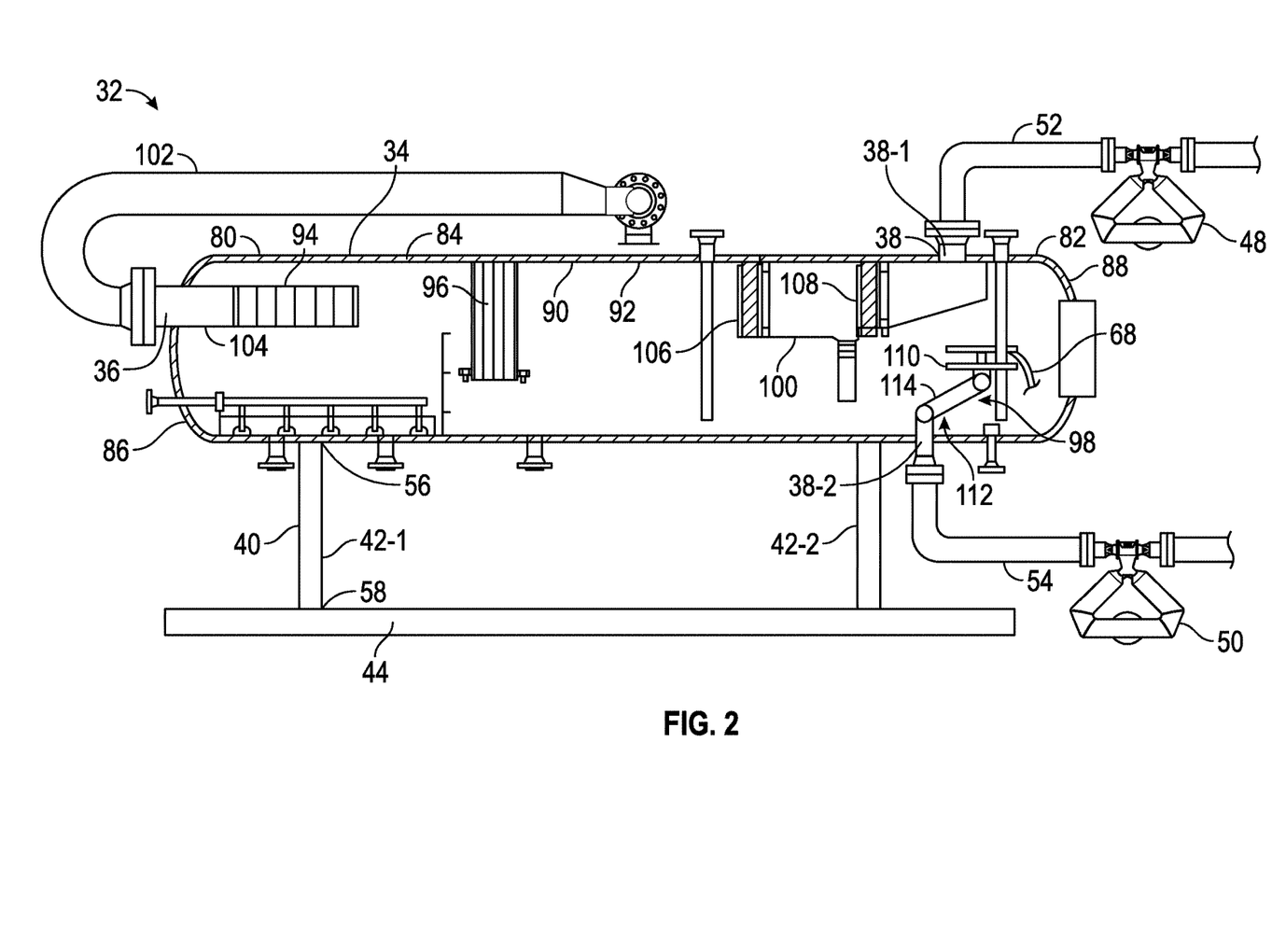
FIG. 2 is a partial cross sectional schematic view of a gas/liquid separator vessel of the separator according to the embodiment of FIG. 1.

Referring now to FIG. 2, the gas/liquid separator vessel 34 is provided with a first end 80, a second end 82, and one or more wall 84 extending therebetween. The gas/liquid separator vessel 34 also includes a first end cap 86 and a second end cap 88. The wall 84 of the gas/liquid separator vessel 34 may be cylindrical in shape. The first end 80 may be connected to the first end cap 86, and the second end 82 may be connected to the second end cap 88, with the first end cap 86 and the second end cap 88 covering the first end 80 and the second end 82, respectively. The gas/liquid separator vessel 34 defines a first separation chamber 90 substantially defined by an interior surface 92 of the gas/liquid separator vessel 34.

At the first inlet 36, the separator 32 may be provided with an inlet device 94. The separator 32 may also include an agglomerator 96, an adjustable collecting assembly 98, and a coalescer and demister assembly 100. Prior to arriving at the inlet device 94, the effluent may travel through an inlet pipe 102. The inlet pipe 102 may be U-shaped, and may be approximately 10 inches in diameter. The U-shape of the inlet pipe 102 may be positioned outside of the gas/liquid separator vessel 34. The inlet device 94 may be connected in series with an inlet piping 104 placed through the first inlet 36 of the gas/liquid separator vessel 34. The inlet device 94 may also be designed to achieve a reduction in the velocity of the effluent and to provide an even gas flow distribution within the gas/liquid separator vessel 34. The inlet device 94 may be, for example, but not by way of limitation, inlet breakers, cyclone clusters, or vane types also called Schoepentoeters. The inlet device 94 may aid in creating more homogeneous downstream gas velocities and present enhanced bulk liquid/mist separation.

The separator 32 may be standardized to a 30 ft (9.14 m) container footprint and with a weight which may not exceed twenty-five tons. The vessel diameter may be restricted by regulations dictated by the transportation authorities. The maximum level of liquid in the tank may be limited by the height of the coalescer and demister assembly 100 in order to maintain a coalescer 106 and a demister 108 above the liquid level. The gas/liquid separator vessel 34 size may be a compromise between effluent capacity and transportability with the separator 32 being transportable from one installation 10 to another. Once both the length and diameter of the separator 32 are determined, the oil retention time should be evaluated. According to the American Petroleum Institute (API), a minimum of 1 minute is recommended to allow the gas dissolved in the liquid to be freed, although this retention time may change in the future as determined by the operator, the well conditions, or industry standard.

The agglomerator 96 may intercept the medium sized liquid droplets carried over with the effluent and form a liquid film flowing along the agglomerator 96 towards the bottom of the gas/liquid separator vessel 34 (coalescence effect). The agglomerator 96 can be formed of coalescer plates made of, as an example but not by way of limitation, several vertical plates assembled as a packing, a vane-type agglomerator 96 or the like.

The adjustable collecting assembly 98 may comprise an oil collector 110, a floating assembly 112, and an oil circuit 114. The floating assembly 112 floats at a gas/liquid interface (GLI). The oil collector 110 may be connected to the floating assembly 112 such that the oil collector 110 remains in an oil layer, just below the GLI. The oil collector 110 may then collect oil-enriched liquid from a thin layer positioned at substantially the same elevation as the oil collector 110. The oil collector 110 may be connected to the oil circuit 114 and the second piping 68, placing the oil circuit 114 and the second piping 68 in fluid communication with the oil layer. The oil circuit 114 may be formed from rigid pipe and swivels, flexible hoses, or any other suitable combination of materials, such that the oil circuit 114 is freely articulable and enables a free vertical position within the gas/liquid separator vessel 34 while maintaining a horizontal position. A portion of the oil drained from the thin layer may flow through the oil circuit 114 to the oil outlet 38-2. Another portion of the oil drained from the thin layer may flow through the second piping 68 to the carry-over meter 46 and the sight glass 60.

Figure 3:
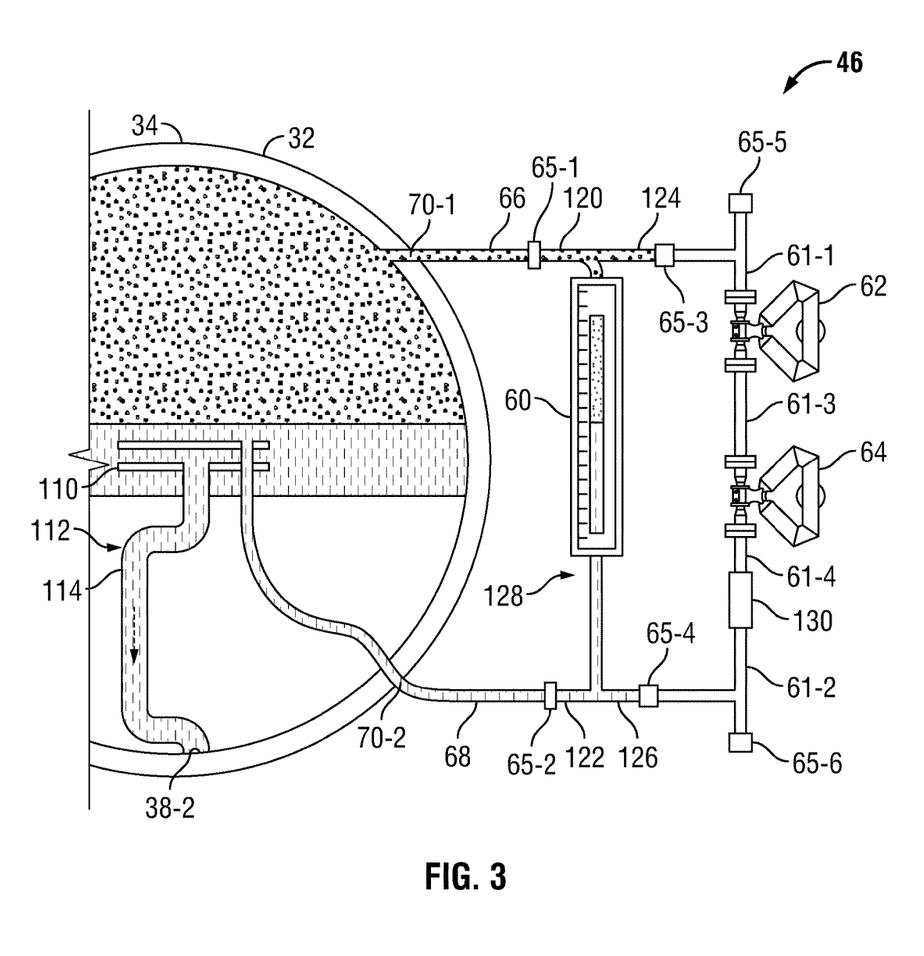
FIG. 3 is a cross sectional schematic view of the gas/liquid separator vessel with an attached carry-over meter, in accordance with the present disclosure.

Referring now to FIG. 3, in one embodiment, the carry-over meter 46 may be positioned on the exterior of the gas/liquid separator vessel 34. The carry-over meter 46 may be provided with the sight glass 60, the sight glass 60 having a first inlet 120, a second inlet 122, a first outlet 124 in fluid communication with the first inlet 120, a second outlet 126 in fluid communication with the second inlet 122, valves 65-1 and 65-2 in fluid communication with the first inlet 120 and the second inlet 122, and a tube 128 extending between the first inlet 120 and the second inlet 122. At least a portion of the tube 128 may be transparent in a visible range of wavelengths.

The first inlet 120 and the second inlet 122 may be in fluid communication with the first separation chamber 90. The first inlet 120 may connect to the first outlet 70-1 via the first piping 66. The second inlet 122 may connect to a second outlet 70-2 via the second tubing 68. The valve 65-1 may be positioned between the first inlet 120 and the first piping 66, and operate to isolate the first inlet 120 from fluid communication with the first separation chamber 90. The valve 65-2 may be positioned between the second inlet 122 and the second piping 68, and operate to isolate the second inlet 122 from fluid communication with the first separation chamber 90. Operating the valves 65-1 and 65-2 in combination may isolate the sight glass 60 from fluid communication with the first separation chamber 90. The first piping 66 connected to the first outlet 70-1 may be in fluid communication with the gas level within the first separation chamber 90 so as to provide fluid communication with a separated gas within the first separation chamber 90. The second piping 68 may be connected to the oil collector 110 such that the second piping 68 and the second inlet 122 may be in fluid communication with the oil level of the first separation chamber 90, so as to provide fluid communication with a separated liquid of the oil layer within the first separation chamber 90. Once effluent enters the first separation chamber 90 and maintains a predetermined level within the first separation chamber 90, the fluid communication between the first inlet 120, second inlet 122, and the first separation chamber 90 allows gas and oil to fill the sight glass 60 of the carry-over meter 46 in a proportion representative of the GLI.

The first densitometer 62 and the second densitometer 64, of the carry-over meter 46, may be connected to the sight glass 60 at the first outlet 124 and the second outlet 126, respectively. The first densitometer 62 may be connected to the first outlet 124 via the valve 65-3 and piping 61-1 such that the first densitometer 62 may be in fluid communication with the first outlet 124 and the first inlet 120, and thereby be in fluid communication with the first separation chamber 90. The valve 65-3 may operate to isolate the first densitometer 62 from fluid communication with the first outlet 124. The second densitometer 64 may be connected to the second outlet 126 via the valve 65-4 and piping 61-2 such that the second densitometer 64 may be in fluid communication with the second outlet 126 and the second inlet 122, and thereby be in fluid communication with the first separation chamber 90. The valve 65-4 may operate to isolate the first densitometer 64 from fluid communication with the second outlet 126. Operating the valves 65-3 and 65-4 to a closed position to a closed position may isolate the first and second densitometers 62 and 64 from fluid communication with the sight glass 60, while allowing the sight glass 60 to remain in fluid communication with the first separation chamber 90. In one embodiment the first densitometer 62 may be in fluid communication with the second densitometer 64 via piping 61-3. The first and second densitometers 62 and 64 may be positioned relative to the sight glass 60, such that the first densitometer 62 may be filled with a separated gas from the sight glass 60 and the second densitometer 64 may be filled with a separated liquid from the sight glass 60. The piping 61-3 may be positioned between the first and second densitometers 62 and 64 to provide distance sufficient for the piping 61-3 to house a gas/liquid interface between the first and second densitometers 62 and 64. Maintaining the gas/liquid interface in the piping 61-3 may ensure that neither the first densitometer 62 nor the second densitometer 64 contain both the separated gas and the separated liquid while performing density measurements. The valves 65-5 and 65-6 may be connected to the piping 61-1 and 61-2 in order to provide bleed-off or completely drain the separated gas and separated liquid contained in the first and second densitometers 62 and 64. The piping 61-1-61-4 may be rigid or flexible and may be formed of metal, plastic, composite, or any other suitable material.

In one embodiment, the carry-over meter 46, comprising the sight glass 60, the first densitometer 62, the second densitometer 64, and the piping 61-1-61-4 may be connected to the gas/liquid separator vessel 34 with suitable outlets but without a sight glass or to replace a sight glass that is incompatible with other embodiments of the carry-over meter 46. In another embodiment, the carry-over meter 46, comprising the first densitometer 62, the second densitometer 64, and the piping 61-1-61-4, may be connected to a gas/liquid separator vessel 34 with an existing sight glass which is compatible with the carry-over meter 46, in order to provide the gas/liquid separator vessel 34 with a suitable carry-over meter 46.

The carry-over meter 46 may also be provided with a vessel 130. The vessel 130 may be connected to piping 61-2 and 61-4 and in fluid communication with the second densitometer 64. In an embodiment where the first densitometer 62 is in fluid communication with the second densitometer 64, the separated gas and separated liquid within the carry-over meter 46 may be isolated within the first and second densitometers 62 and 64 and given a predetermined time to separate. The further separation of the separated gas may cause entrained liquid to be recovered from the separated gas. The vessel 130 may provide a volume to recover the entrained liquid recovered from the separated gas within the first densitometer 62. In one embodiment the vessel 130 may be 50 cc. However it will be understood by one skilled in the art that the vessel 130 may be of any suitable size and shape to be in fluid communication with the first and second densitometers 62 and 64 and provide sufficient volume to receive liquid recovered from the separated gas.

The first and second densitometers 62 and 64 may comprise Coriolis meters similar to the first and second Coriolis meters 48 and 50. In one embodiment, the first densitometer 62 and the second densitometer 64 may comprise Coriolis meters adapted to measure lower mass flow rates and densities and provide more precise calibration for a smaller flow rate, volume, or pressure of fluid within the Coriolis meters than those provided for the first and second Coriolis meters 48 and 50.

Figure 4:
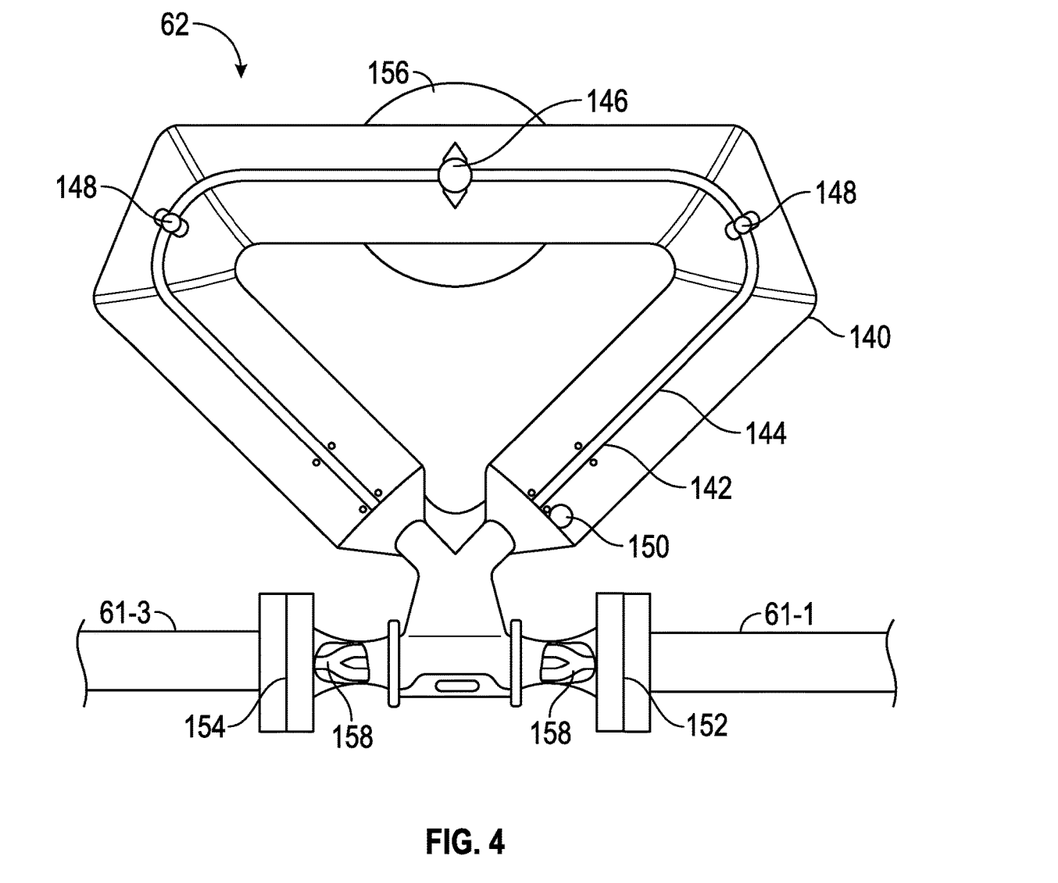
FIG. 4 is a partial cross sectional elevational view of a Coriolis meter of the carry-over meter depicted in FIG. 3.

Referring now to FIG. 4, the first and second densitometers 62 and 64 may be identical in construction and function for purposes of brevity, the first densitometer will be described herein. However it should be understood that said description is applicable to the second densitometer 64. The first densitometer 62 may be curved tube Coriolis meters or straight tube Coriolis meters. In the embodiment where the first densitometer 62 is a curved tube Coriolis meter, the first densitometer 62 may be provided with a housing 140, a first flow tube 142 and a second flow tube 144 within the housing 140, a drive coil 146 and a pickoff coil 148 connected to one or more of the first flow tube 142 and the second flow tube 144, a resistance thermal device 150, a first process connection 152 and a second process connection 154 in fluid communication with the first flow tube 142 and the second flow tube 144, and a core processor 156. The first and second flow tubes 142 and 144 may be wetted parts, directly exposed to oil or gas, and constructed from stainless steel or nickel alloy depending on compatibility with the effluent passing through the first and second flow tubes 142 and 144, such as resistance to corrosion forces within the effluent.

The drive coil 146 may be used with a magnet to produce oscillation within the first flow tube 142 and the second flow tube 144. The oscillation of the first flow tube 142 and the second flow tube 144 may be substantially similar, without intervening Coriolis forces caused by fluid within the first and second flow tubes 142 and 144. The oscillation may cause vibration in the first and second flow tubes 142 and 144 at a constant amplitude in the range of 0.5 to 2 mm.

The pickoff coils 148 may comprise one or more magnets and one or more electromagnetic detectors. The pickoff coils 148 may be connected to both the first flow tube 142 and the second flow tube 144 and positioned between the first and second flow tube 142 and 144 such that the pickoff coils 148 on the first flow tube 142 face the pickoff coils 148 on the second flow tube 144. The pickoff coils 148 may produce a signal representative of the velocity and position of the first and second flow tubes 142 and 144 at a given point in the oscillation. The mass flow may be determined by measuring the phase difference between these signals, comparing the phase difference between the signals produced by two or more pickoff coils 148 located along the first and second flow tubes 142 and 144.

The resistance thermal device 150 may provide an output signal of the temperature of the first and second flow tubes 142 and 144. The resistance thermal device 150 may comprise a 100 ohm platinum element, strain free element, thin film element, wire-wound element, or coiled element, for example.

The first process connection 152 and the second process connection 154 may be end connections or fittings. The first and second process connections 152 and 154 may connect between one or more of the piping 61-1-61-4. The first and second process connections 152 and 154 may be mated to the piping 61-1-61-4 such that the fluid passing through the piping 61-1-61-4, into the first and second densitometers 62 and 64 remains within the fluid flow path without leaks. Within the first process connection 152 and the second process connection 154 may be a flow splitter 158. The flow splitter 158 may divide the fluid passing into the first and second densitometers 62 and 64 evenly between the flow tubes.

The core processor 156 may be connected to the drive coil 146, the pickoff coils 148, and the resistance thermal device 150 via wiring contained within the housing 140. The core processor 156 may execute calculations to measure values, such as fluid flow rate, mass flow rate, and density of the fluid within the first densitometer 62. The core processor 156 may be implemented as one or more digital signal processors, or any other suitable processor. The core processor 156 may be connected to a one or more non-transitory computer readable medium (not shown) for storing computer executable instructions related to the function of the first densitometer 62 and for storing measurements taken by the first densitometer 62, one or more filters (not shown) for processing measurements taken by the first densitometer 62 to aid in the conversion and communication of the measurements, one or more output processor (not shown) for converting measurements taken by the first densitometer 62 into user output signals for transmission by a communications device, one or more communications device (not shown) for communicating measurements taken by the first densitometer 62 a user.

Figure 5:
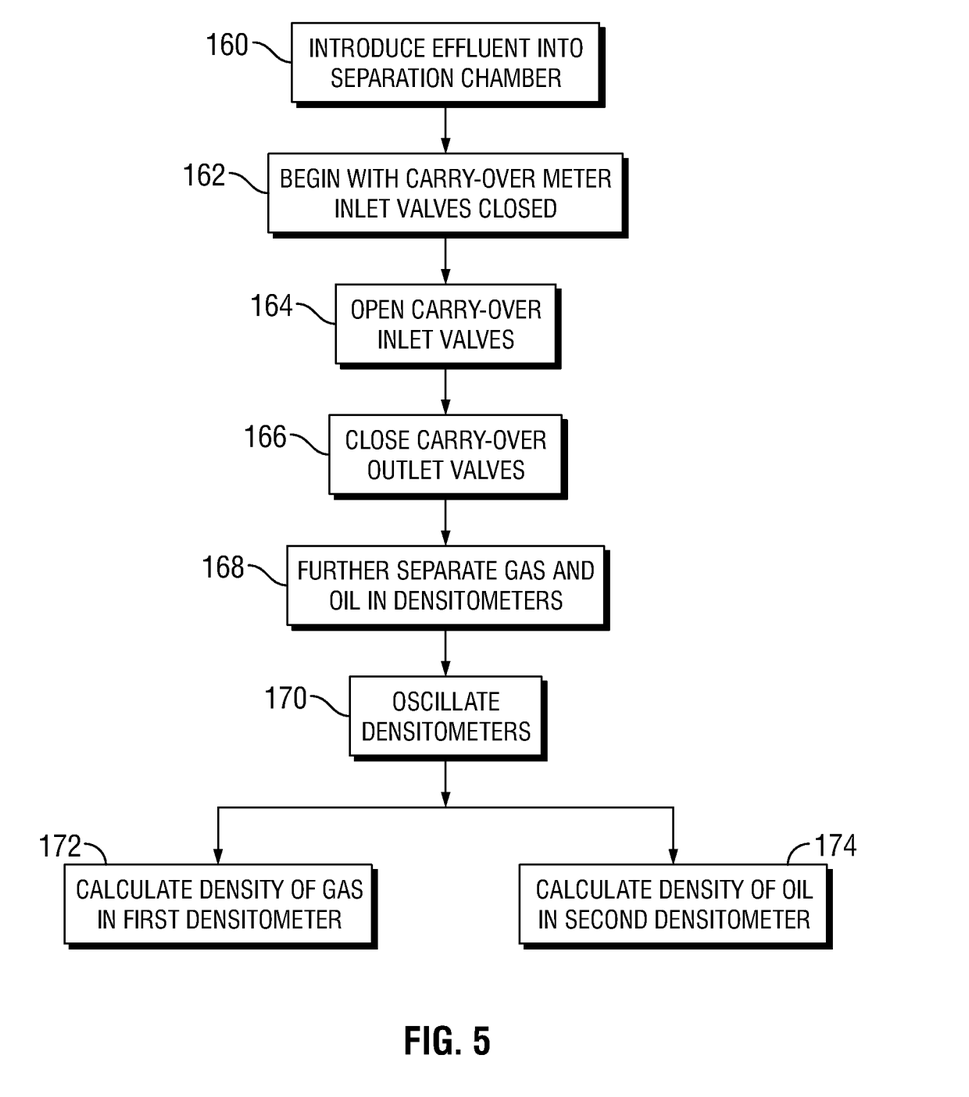
FIG. 5 is a flow diagram of a process for measuring density using the carry-over meter in accordance with an embodiment disclosed in the present disclosure.

Referring now to FIG. 5, the first densitometer 62 and the second densitometer 64 may be used to measure the density of gas and oil settled and separated from the effluent. The effluent may be introduced into the first separation chamber 90 at 160 and may initially separate into gas and liquid layers, with the liquid layers separating into oil and water layers. The valves 65-1 and 65-2 may begin in a closed position, at 162, so that as the effluent fills the first separation chamber 90 and separates into gas and oil, without the fluid from the gas and oil layers entering the first inlet 120 and the second inlet 122, respectively, of the sight glass 60. Once the separated gas and oil reaches a predetermined level within the first separation chamber 90, the valves 65-1 and 65-2 may be opened, at 164, to allow fluid communication between the first separation chamber 90, the sight glass 60, and the first and second densitometers 62 and 64. Once the separated gas and oil fill the sight glass 60 and the first and second densitometers 62 and 64, the valves 65-3 and 65-4 may then be closed to isolate the first and second densitometers 62 and 64, at 166. The gas and oil contained in the first and second densitometers 62 and 64 may be afforded a predetermined time to settle and further separate by gravity separation, at 168. After the predetermined settling time at 168, the first and second densitometers 62 and 64 may be engaged, so that a drive coil within the first and second densitometers 62 and 64 may cause flow tubes within the respective first and second densitometers 62 and 64 to oscillate, at 170. A core processor (e.g. the core processor 156) within the first and second densitometer 62 and 64 may calculate the density of the separated gas within the first densitometer 62, at 172, and the separated oil within the second densitometer 64, at 174, by comparing the difference between the expected period of oscillation of the flow tubes and the actual period of oscillation of the flow tubes filled with gas or oil.

The densities of the separated gas and oil, determined using the carry-over meter 46 as described above, may be used in determining the Liquid Volume Fraction (LVF) of the separated gas flowing through the gas outlet pipe 52 after being separated from the effluent by passing through the gas/liquid separator vessel 34. When the valves 65-1 and 65-2 are closed and the sight glass 60 contains gas and oil, the volume of the fluid contained in the sight glass 60 and the flow tubes of the first and second densitometer 62 and 64 remains constant, therefore the mass of the fluid may not change if the density remains unchanged. Due to the relationship between mass and density, the density of the fluid contained within the flow tubes can be determined if the mass of the fluid is known. The period of oscillation of the flow tubes may be measured in microseconds per cycle, for example. Because of the predetermined settling time, discussed above, the density measurements for the gas and oil, taken by the first and second densitometers 62 and 64, respectively, may be used as clean oil density and clean gas density at the ambient conditions of the gas/liquid separator vessel 34. The first densitometer 62 therefore measures the gas density at separator conditions $\rho_g$ (kg/m$^3$), and the second densitometer 64 measures the oil density $\rho_l$ (kg/m$^3$). The first Coriolis meter 48 may provide the mixture density $\rho_m$ of the gas and carry over liquid at the gas outlet pipe 52 and the mass flow rate $Q_{m_{Co}}$ (kg/s). From these variables, the LVF may be calculated to give a measurement of the liquid carry-over, the liquid remaining within the separated gas stream after passing through the separator 32. The LVF of the gas and carry over liquid mixture at the gas outlet pipe 52 of the gas/liquid separator vessel 34 may be calculated using the gas density from the first densitometer 62, the liquid density from the second densitometer 64, and the mixture density from the first Coriolis meter 48 by using Equation 1: $\rho_m = \text{LVF}\, \rho_l + (1-\text{LVF})\, \rho_g$.

Although a few embodiments of the present disclosure have been described in detail above, those of ordinary skill in the art will readily appreciate that many modifications are possible without materially departing from the teachings of the present disclosure. Accordingly, such modifications are intended to be included within the scope of the present disclosure as defined in the claims.

What is claimed is:

1. A separator comprising: a gas/liquid separator vessel having an exterior and defining a separation chamber therein, the separation chamber having a first outlet, a second outlet, a third outlet, and a fourth outlet; a first densitometer connected to the first outlet of the separation chamber; a second densitometer connected to the second outlet of the separation chamber; a sight glass positioned on the exterior of the gas/liquid separator vessel, the sight glass to contain a separated gas, the sight glass having a first inlet in fluid communication with the third outlet of the separation chamber and a second inlet in fluid communication with the fourth outlet of the separation chamber, the sight glass having a first outlet in fluid communication with a third densitometer, and a second outlet in fluid communication with a fourth densitometer, the sight glass having a tube extending between the first inlet and the second inlet of the sight glass; a pipe conduit disposed between the third and the fourth densitometers; and a first isolation valve between the third densitometer and the first outlet of the sight glass and a second isolation valve between the fourth densitometer and the second outlet of the sight glass.

2. The separator of claim 1, wherein the first inlet of the sight glass is in fluid communication with the separation chamber at a level to provide fluid communication with the separated gas within the separation chamber.

3. The separator of claim 1, wherein the second inlet of the sight glass is in fluid communication with the separation chamber at a level providing fluid communication with a separated liquid within the separation chamber.

4. The separator of claim 1, wherein the first densitometer is a first Coriolis meter, the second densitometer is a second Coriolis meter, the third densitometer is a third Coriolis meter, and the fourth densitometer is a fourth Coriolis meter.

5. The separator of claim 1, wherein the third densitometer is connected to the third outlet of the separation chamber and positioned at a level providing fluid communication with the separated gas within the sight glass.

6. The separator of claim 1, wherein the fourth densitometer is connected to the fourth outlet of the separation chamber and positioned at a level providing fluid communication with a separated liquid within the sight glass.

7. The separator of claim 1, wherein the first and second valves operate in combination to isolate the third and fourth densitometers from fluid communication with the sight glass.

8. The separator of claim 1, further comprising a vessel positioned between the fourth densitometer and the second outlet of the sight glass, the vessel in fluid communication with the fourth densitometer to recover the liquid from the separated gas within the third densitometer.

9. The separator of claim 1, wherein at least a portion of the tube is transparent to light in a visible range of wavelengths.

10. The separator of claim 1, wherein the conduit is to maintain a gas/liquid interface to ensure that neither the third densitometer nor the fourth densitometer contains both the separated gas and a separated liquid while performing a measurement.

11. A carry-over meter, comprising:
a sight glass having a first inlet, a second inlet, a first outlet in fluid communication with the first inlet, a second outlet in fluid communication with the second inlet, and a tube extending between the first inlet and the second inlet, the sight glass to contain a separated gas;
a first densitometer connected to the first outlet and a second densitometer connected to the second outlet with the first and second densitometers in fluid communication with the sight glass; and
a conduit disposed between the first and the second densitometers;
a first isolation valve disposed between the first densitometer and the first outlet;
a second isolation valve disposed between the second densitometer and the second outlet;
a third valve connected to the first densitometer; and
a fourth valve connected to the second densitometer.

12. The carry-over meter of claim 11, further comprising a vessel positioned between the second densitometer and the second outlet, the vessel in fluid communication with the second densitometer to recover the liquid from the separated gas within the first densitometer.

13. The carry-over meter of claim 11, wherein the first densitometer is a first Coriolis meter and the second densitometer is a second Coriolis meter.

14. The carry-over meter of claim 11, wherein at least a portion of the tube is transparent to light in a visible range of wavelengths.

15. The carry-over meter of claim 11, wherein the conduit is to maintain a gas/liquid interface to ensure that neither the first densitometer nor the second densitometer contains both the separated gas and a separated liquid while performing a measurement.

16. A carry-over meter comprising:
a first densitometer having a first inlet and a first outlet, the first densitometer to contain a separated gas;
a second densitometer having a second inlet and a second outlet, the second inlet connected to the first outlet, and the first inlet and second outlet connectable to a vessel, thereby forming a closed loop when connected to the vessel;
a pipe disposed between the first and the second densitometers to separate a flow of liquid contained in the separated gas from the first densitometer to the second densitometer by gravity separation;
a first valve connected to the first inlet of the first densitometer and in fluid communication therewith;
a second valve connected to the second outlet of the second densitometer and in fluid communication therewith;
a first isolation valve connected to the first inlet of the first densitometer; and
a second isolation valve connected to the second outlet of the second densitometer.

17. The carry-over meter of claim 16, further comprising a vessel positioned between the second densitometer and the second valve, the vessel in fluid communication with the second densitometer to recover the liquid recovered from the separated gas within the first densitometer.

18. The carry-over meter of claim 16, wherein the first densitometer is a first Coriolis meter and the second densitometer is a second Coriolis meter.

* * * * *